US006424996B1

(12) United States Patent
Killcommons et al.

(10) Patent No.: US 6,424,996 B1
(45) Date of Patent: Jul. 23, 2002

(54) MEDICAL NETWORK SYSTEM AND METHOD FOR TRANSFER OF INFORMATION

(75) Inventors: Peter M. Killcommons; Lawrence Foard, IV, both of San Francisco, CA (US)

(73) Assignee: Nexsys Electronics, Inc., San Francisco, CA (US)

( * ) Notice: Subject to any disclaimer, the term of this patent is extended or adjusted under 35 U.S.C. 154(b) by 0 days.

(21) Appl. No.: 09/199,611

(22) Filed: Nov. 25, 1998

(51) Int. Cl.[7] .............................................. G06F 17/60
(52) U.S. Cl. ........................ 709/206; 709/218; 345/331; 382/128
(58) Field of Search ................................ 707/100, 104; 705/2; 709/217, 218, 219, 206, 207; 345/326, 330, 331; 382/100, 128

(56) References Cited

U.S. PATENT DOCUMENTS

| 5,321,520 | A | * | 6/1994 | Inga et al. .................... 358/403 |
| 5,469,353 | A | * | 11/1995 | Pinsky et al. ................. 382/131 |
| 5,586,262 | A | * | 12/1996 | Komatsu et al. ................. 705/2 |
| 5,668,998 | A | * | 9/1997 | Mason et al. ................. 395/701 |
| 5,715,823 | A | * | 2/1998 | Wood et al. .................. 600/437 |
| 5,740,428 | A | * | 4/1998 | Mortimore et al. .......... 707/104 |
| 5,867,821 | A | * | 2/1999 | Ballantyne et al. ............. 705/2 |
| 5,924,074 | A | * | 7/1999 | Evans ............................ 705/3 |
| 5,950,207 | A | * | 9/1999 | Mortimore et al. .......... 707/104 |
| 5,986,662 | A | * | 11/1999 | Argiro et al. ................. 345/424 |
| 5,988,852 | A | * | 11/1999 | Nakanishi ..................... 700/83 |

FOREIGN PATENT DOCUMENTS

| WO | 97/18675 | 10/1997 |
| WO | 97/21747 | 12/1997 |
| WO | 99/28085 | 11/1999 |

OTHER PUBLICATIONS

Abate, Tom, "Entrepreneures Discover Internet", San Francisco Examiner, Business Section, May 29, 1994, entire article.*

"MedWeb Plugin Turns Netscape Browser into a Medical Imaging Workstation; MedWeb Radiology Workstation Plugin Saves Hospitals Millions of Dollars", Business Wire, Dec. 4, 1996, entire article.*

Abate, Tom, "Setting Up Shop on the Internet Entrepreneurs Explore It's Commercial Potential", San Francisco Examiner, Business Section, Jul. 14, 1994.*

Thrall JH, Boland G., "Telemedicine in Practice," Seminars in Nuclear Medicine 28(2): 145–57, Apr. 1998.

(List continued on next page.)

*Primary Examiner*—Dung C. Dinh
(74) *Attorney, Agent, or Firm*—Blakely, Sokoloff, Taylor & Zafman LLP

(57) ABSTRACT

The assembly and communication of multimedia information from a variety of modalities to remote users with improved control is provided for by the combined use of a browser enhancement module, such as a plug-in or ActiveX control, and a server. The server includes a data interface for acquiring the multimedia data and a storage unit for receiving and storing the data. An assembly unit in the server gathers selected data to form an e-mail package in response to instructions from a remote user unit. The server further includes a processing unit to encode and compress the data prior to packaging and an e-mail server to send the package to the remote user unit or another designated user unit. Transfer instructions for the server may be provided by the remote user unit through a browser and the browser enhancement module. The browser enhancement module is therefore configured to request a file from the server, to decompress and decode received files and to transfer such files along with a user interface to a display associated with the remote user unit. The browser enhancement module is further adapted to send instructions to the server to assemble and to e-mail selected data from a file to another user unit.

58 Claims, 4 Drawing Sheets

OTHER PUBLICATIONS

Bidgood et al., "Understanding and Using DICOM, the Data Interchange Standard for Biomedical Imaging," J.Am. Med. Informatics Assoc., 4:3, 199–122, May–Jun., 1997.

Pruna S et al., "Black Sea Teldiab: diabetes computer system with communication technology for Black Sea region", ITAB '97., Proceedings of the IEEE Engineering In Medicine and Biology Society Region 8 International Conference (CAT. No. 97TH8342), Prague, Czech Republic, pp. 11–13, Sep. 1997.

Dayhoff R E et al., "Mechanisms for Exchange of Image Data to Support Distant Medical Consultation," Proceedings of Seventeenth Annual Symposium On computer Applications In medical Care, Washington, DC, USA., pp. 808–812, Oct. 30–Nov. 3, 1993.

Haufe G et al., "PACS at work: a multimedia e–mail tool for the integration of images, voice and dynamic annotation," Proceedings of The International Symposium On Computer and Communication Systems for Image Guided Diagnosis and Therapy, Proceedings of CAR'96: Computer Assisted Radiology—10th International Symposium, Pars, France., pp. 417–420, Jun. 1996.

Pira R S et al., "Supporting Asynchronous Telemedicine: Multimedia Mail vs. The World Wide Web vs. Replicated Databases," Conference Proceedings IEEE Canadian Conference on Electrical and Computer Engineering, Waterloo, Ont., Canada, pp. 341–344, May 24–28, 1998.

Bitti M G et al., "A WWW–Based Distributed System for Medical Data Analysis and 3D Reconstruction," Computer Assisted Radiology., Proceedings of the International Symposium,, pp. 345–350, Jun. 1, 1996.

"Medweb Plug–in", Medweb Distributed Medicine, Medweb, 1996.

"Medweb's Teleradiology Plug–in, Software Manual for use with Windows 95", Medweb Distributed Medicine, Medweb, 1996.

"Integrated Solutions Catalog", Medweb Distributed Telemedicine, Medweb, Apr. 1997.

Computer Dictionary, Third Edition, Microsoft Press, 1997, p. 268.*

* cited by examiner

MEDICAL NETWORK SYSTEM AND METHOD FOR TRANSFER OF INFORMATION

NOTICE OF COPYRIGHT

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates generally to the transfer of multimedia information through the Internet, and more particularly to an integrated e-mail and server system for manipulating and communicating medical information.

BACKGROUND

In many fields (e.g., medicine, manufacturing, veterinary science, scientific research, etc.), it is often necessary to examine a subject and communicate the results of the examination to a remote place. Such information exchanges are especially desirable in the medical arena where it is often useful for medical practitioners to communicate medical information, such as patient test results, to other practitioners located in remote places. Telemedicine facilitates this exchange of information.

Telemedicine is an emerging field that enables medical knowledge to be shared amongst a variety of users that need not be co-located. Interest in telemedicine has exploded in the 1990's with the development of medical devices for capturing data in digital electronic form and the establishment of high speed, high bandwidth telecommunication systems around the world. In particular, the use of the Internet in telemedicine allows a practitioner at one location to interpret medical test results and consult with another practitioner located elsewhere. Medical information transfer systems that employ the Internet allow for remote locations, such as third world countries that do not have an attending specialist, to access such medical expertise. Furthermore, emergency care may be provided where a practitioner is temporarily away, e.g., at home or on vacation. See, e.g., Thrall JH, Boland G., "Telemedicine in practice", Seminars in Nuclear Medicine 28(2):145–57, April 1998.

Medical information (e.g., as may be utilized by a telemedicine system) may be derived from many different medical modalities. Such modalities may include sophisticated radiology equipment grouped as small matrix size and large matrix size instruments. Small matrix systems include equipment for magnetic resonance imaging (MRI), computed tomography (CT), ultrasonography (US), nuclear medicine (NM) and digital fluorography. Large matrix systems include equipment for computer radiography (CR) and digitized radiography (DR). Other data image acquisition equipment may be used for radiofluoroscopy, angiography, such as x-ray angiography and heart scanning. Still other equipment of great usefulness in acquiring medical information includes secondary capture devices for video, endoscopy, microscopy, and photography, such as digital cameras, scanners, electrocardiogram (ECG) machines, and the like.

The resulting medical information may take numerous forms, including text, images and video, or variations thereof, such as image overlay data, measurements, coordinates, etc. Information may also be in the form of time-dependent data including sound, such as audio dictation, and waveform data. The data may be static representations of timedependent forms, such as curves. Thus, it is advantageous for telemedicine systems that may need to transfer the data and/or information to be flexible, so as to accommodate this variety of information/data from multiple modalities.

Unfortunately, this type of flexibility is not exhibited in current systems. For example, some current medical information transfer systems have integrated medical modalities to not only generate data but also to capture data signals, to store the data and to transmit the data over the Internet. Typically, in such systems the modality has an integrated Web server, storage database and Web pages as physical parts of the modality system. A remote Web browser is allowed to request data from the modality through the Internet (e.g., via the World Wide Web) and the Web server in the modality is allowed to respond accordingly. One such system, which has restricted applicability to ultrasound machines, is described in U.S. Pat. No. 5,715,823.

One drawback of such systems is that individual Web servers are required for each medical modality unit, making it a costly endeavor to share data among a number of practitioners. Furthermore, each server is limited in use to only the attached type of medical modality.

Other systems for transferring medical files are adapted to accept data from a variety of modalities, but require an interface to convert data into transferable signals. One such system described in WO 98/24358 converts system binary file data from a modality to a compatible file of keystroke codes using an adapter. The codes are transferred to a computer, which converts the codes to American Standard Code for Information Interchange ("ASCII") characters for transmission over the Internet to a host computer. This multiple file conversion process is an unnecessary burden, however, as current Internet technology does not require that information be converted into ASCII format. Presently, the Internet accepts binary Extended Binary Coded Decimal Interchange Code ("EBCDIC") and ASCII codes. Thus, an ASCII adapter is now an unnecessary extra device for transmitting medical data.

In addition to simply receiving the medical information, it is often important that a practitioner receive the information in a timely manner, especially where a quick diagnosis needs to be rendered for patient care. Thus, it is advantageous for telemedicine systems to rapidly transfer medical data. As noted, some current telemedicine systems rely on the Internet (i.e., as accessed through its graphically-oriented user interface, the World Wide Web) to transfer information. However, current Web-based transfer systems often suffer from long delays in downloading Web pages having complex data, such as large images. This presents a particular problem for the rapid sharing of medical information as a typical MRI study, for example, may have over 100 images, each of which may be 300 to 500 Kb in size, loading to a study of 50 to 80 Mb total.

These transfer times may be enhanced by compression of the data prior to transmission over the Internet. Traditional compression schemes (e.g., JPEG, GIF and bitmap schemes), however, tend to operate at low efficiencies. Such low compression efficiency may only provide for transfer of simple data before significant resolution losses and/or the truncation of data segments is/are experienced. With the use of high efficiency compression methodologies, such as wavelet compression techniques, transfer times can be reduced twenty fold. Unfortunately, however, the use of such high compression efficiency schemes is not prevalent among current telemedicine systems.

Another approach to solving the dilemma of lengthy transfer times is with the use of electronic mail ("e-mail"). E-mail provides a user with apparently instant transfer times, because information is sent as a package in advance. Using e-mail, studies may be "pushed" to the user so that the files are already available at the user's computer when the user is ready to view the data. By contrast, when a user requests a Web page through a browser, each page must be separately downloaded.

Some current e-mail technologies allow for the point-to-point transfer of a variety of data from different modalities. However, these systems do not operate with a central storage system. Without a server database, the operations are limited. For example, one may not retrieve information about how multiple images relate to one another. Such relationship information is essential for studying data from certain modalities, such as radiology images, and is required for compliance with some medical industry standards, e.g., the multi-specialty DICOM Standards (as originally published by an ACR-NEMA committee sponsored by the American College of Radiology and the National Electrical Manufacturers Association as Digital Imaging and Communications in Medicine (DICOM), NEMA Publications PS 3.1–PS3.12., by The National Electrical Manufacturers Association, Rosslyn, Va., 1992, 1993, 1994, 1995).

The DICOM Standards define the form and flow of electronic messages that convey images and related information between computers. Therefore, it is desirable for medical information transfer systems to acquire and transmit complex data, such as radiology images, in a manner that complies with DICOM standards. See, e.g., Bidgood, et al., "Understanding and Using DICOM, the Data Interchange Standard for Biomedical Imaging," J. Am. Med. Informatics Assoc., 4:3, 199–212, May–June, 1997. As indicated, however, some systems do not meet this requirement.

Other medical e-mail systems are limited to purely textual data forms. An example of a medical information transfer system of this type is described in WO 98/16893. This system allows a service request to be sent by one operator through a client system to another operator at a sponsor system. The request may be for some action to be performed by the operator at the sponsor system, such as to perform a test, or to provide authorization therefor, and the like. Although perhaps useful, these textual systems are not designed to transfer complex data, such as images and multimedia output, generated by many medical modalities.

Thus, in light of the shortcomings of the various currently available systems, there is still a need for medical transfer systems that allow for transfer of complex data from a variety of modalities over e-mail and web browser systems.

SUMMARY OF THE INVENTION

In one embodiment, a medical information transfer server is provided. The server is adapted to store multimedia medical data (e.g., parameter and/or clinical data) and includes a data interface for acquiring the medical data; a storage unit coupled to the data interface and configured to receive and store the medical data; and a user interface (e.g., a Web page) for viewing the medical data. In some cases, individual storage subunits may be used for storage of the parameter and clinical data, respectively. An assembly unit may be coupled to the user interface, the storage unit and/or the data interface. The assembly unit may be used to gather selected portions of the stored medical data (and/or new data) to form an e-mail package. In some cases, such actions may be undertaken in response to instructions from a remote user unit. Often, the server will include a processing unit, which may be coupled to the assembly unit or the data interface, configured to encode, compress and/or encrypt the medical data (e.g., prior to the data being assembled into an e-mail package, or even prior to being stored). In other configurations, separate processing units may be used for some or all of these functions. In any event, various compression schemes may be employed, such as progressive compression schemes, wavelet, motion wavelet, MPEG and/or motion JPEG schemes, and the like. In the progressive schemes, any suitable compression algorithm may be used in a looping fashion to compress the data to a desired or acceptable size. An e-mail server configured to send the user interface and the e-mail package to the remote user unit and/or another user unit may also be included. The multimedia medical data stored by the server may be text, image, overlay, 3-D volume, waveform, curve, video or sound data, or any combination thereof.

The server may further include a 3-D volumetric rendering element and/or a 3-D surface rendering element for converting 2-D images into 3-D images. Window and/or level controls may be included for establishing window and/or level default values. In some cases, an automatic e-mail control may be included to direct the e-mail server to automatically send any new medical data to the remote user unit at prescribed intervals.

Another embodiment provides a medical information transfer unit that includes a display for viewing a medical file on a user interface having at least one manipulation element for view control of the medical file, and a browser for communicating with a server having stored therein a plurality of medical files containing multimedia medical data. The browser includes a browser enhancement module configured to request a medical file from the server; decompress, decode and/or decrypt the medical file (if necessary); transfer the medical file to the display; and/or send instructions to the server to assemble and to e-mail selected medical data from the medical file (which may include clinical data, parameter data, series data, annotation data, observation data, 3-D volume data, and/or combinations thereof) to a remote user unit that is separate from the transfer unit.

The browser enhancement module may be a plug-in or an ActiveX control, where appropriate. Further, it may be configured to instruct the server to assemble selected data with new data to form a package and to e-mail the package to the remote user unit. This new data may be originally acquired by the transfer unit through an associated modality interface.

Still other embodiments may provide a computer readable medium having stored therein a plurality of sequences of instructions, which when executed by a processor, cause the processor to perform certain steps (e.g., through the use of a browser or otherwise). Among these steps may be included the steps of requesting from a server a medical file on a user interface having at least one manipulation element for view control of the medical file, the server having stored therein medical files containing multimedia medical data; decompressing, decoding and/or decrypting the medical file; transferring the medical file to a display; and/or e-mailing instructions to the server to assemble and send selected medical data from the medical file from the server to a remote user unit which is separate from the processor. The medical data may be in the form of text, image, overlay, 3-D volume, waveform, curve, video or sound data, or any combination thereof. Of course, other embodiments may provide only the instructions themselves or the instructions as carried in a data signal by a carrier wave.

According to still further embodiments, multimedia information from a variety of modalities may be assembled and communicated to remote users with improved control by the combined use of a browser enhancement module, such as a plug-in or ActiveX control, and a server. A remote user unit that includes the browser enhancement module may access and manipulate data stored in the server by sending instructions thereto. In some cases, communication is achieved, at least in-part, through an e-mail system integrated with the server, where the server assembles and sends the e-mail package. By this design, a user may transfer information stored on the user's computer, but is not limited to e-mail transfers of such stored information. Rather, the user may access and congregate a variety of information from different sources (such as the server) or instruct the server to retrieve useful data from other remote hosts, thereby providing the user or another receiving party with a comprehensive package of information.

The benefits of information storage on the server are direct in that the type of information available to a user is flexible and may be in compliance with the DICOM Standards. In one embodiment, portions of data files are related to other portions of files stored on the server. The server may also store associated information such as specific parameters used by a modality in deriving medical data, notes and observations made by a practitioner, as well as patient histories.

Other embodiments further provide for sophisticated manipulation of data (e.g., medical information). Requested data may be received by a user unit through a user interface, such as a Web page, from a server. The user interface may provide a wide selection of view controls for optionally manipulating the manner in which data is displayed. Some or all of these controls may be included in a browser enhancement module, which may make up a portion of the user interface (with the remaining portion of the user interface being stored at the server). The server may additionally have controls such as 3-D image rendering device to allow for further viewing enhancements.

In still a further embodiment, a server and/or a browser enhancement module may be configured to receive complex data from a variety of sources. To avoid truncation during transmission of large data files, such as radiology files with numerous images, high level compression schemes, e.g. wavelet compression schemes, may be employed to reduce the size of any transferred data files. In some cases, the enhancement module may be configured to acquire and/or encode new medical data directly from a medical modality. The enhancement module may pass such new medical data to the server along with specific instructions regarding how the server is to handle the data. For example, the enhancement module may instruct the server to assemble the new data with data stored on the server and send the resulting package to another remote user. In addition, the enhancement module may be configured to direct the operation of a remote medical modality in deriving medical data.

Other features and advantages of these and other embodiments are discussed in detail below.

BRIEF DESCRIPTION OF THE DRAWINGS

The present invention is illustrated by way of example, and not limitation, in the figures of the accompanying drawings in which:

FIGS. 2A–2D are block diagrams of various embodiments of a server configured in accordance with the teachings presented herein, wherein FIG. 2A shows a server where new data is compressed prior to storage, FIG. 2B shows a server where new data is stored without prior compression, FIG. 2C shows a server where new data is assembled and then stored and FIG. 2D shows a server where new data is assembled and then processed as well as stored.

DETAILED DESCRIPTION

The Medical Network System and Method for Transfer of Information described below is configured to provide a rich variety of image manipulation, viewing and annotation tools for review of information and transfer of the information to remote users. The system utilizes browser and/or e-mail enhancement units, such as may be embodied in a plug-in for Netscape-brand browser interfaces (e.g., Netscape Navigator) or MIME interfaces, or an ActiveX control for a Microsoft-brand browser interfae (e.g., Internet Explorer), to provide this rich application environment. By incorporating advanced functionality into a down-loadable browser enhancement unit, a user need only have available basic computer equipment, such as an off-the-shelf personal computer (PC) equipped with an Internet browser. Furthermore, the integrated functionality provided by the present system allows correspondents anywhere on the Internet to instantly have the same tool kit.

The data that is transferred by the operator of a server configured in accordance with the present teachings may take numerous forms. Some common formats include text, images, video, sound, such as audio dictation, waveform, curves, and/or combinations or variations thereof. Moreover, although the data may pertain to the examination of a subject in any number of fields, such as manufacturing, veterinary science, scientific research, etc., the data is preferably medically related to a subject's physical condition. Medical data of this sort may be grouped into various types. Clinical data is information acquired by a medical modality during the examination of a patient and relates to the patient's physical health. Examples of clinical data may include radiology images, camera photographs, sound recordings, and the like. Parameter data is another type of data representing criteria surrounding the acquisition of clinical data. Parameter data includes the settings of the medical modality acquiring the clinical data, relationships of multiple sets of data such as overlay data, timing of the data acquisition, measurements, coordinates, and the like. The parameter data includes some of the information required by the DICOM Standards for stored and transferred medical files. Other medical data may include 3-D volume data; series data for all clinical data in a medical series, e.g., coronal slices vs. axial slices in a CT exam or echoes as T1 slices vs. T2 slices in an MRI exam; annotation data for notes made by a practitioner, usually relating to the clinical data; and background data such as patient history and/or physical examination information.

Figure 1:
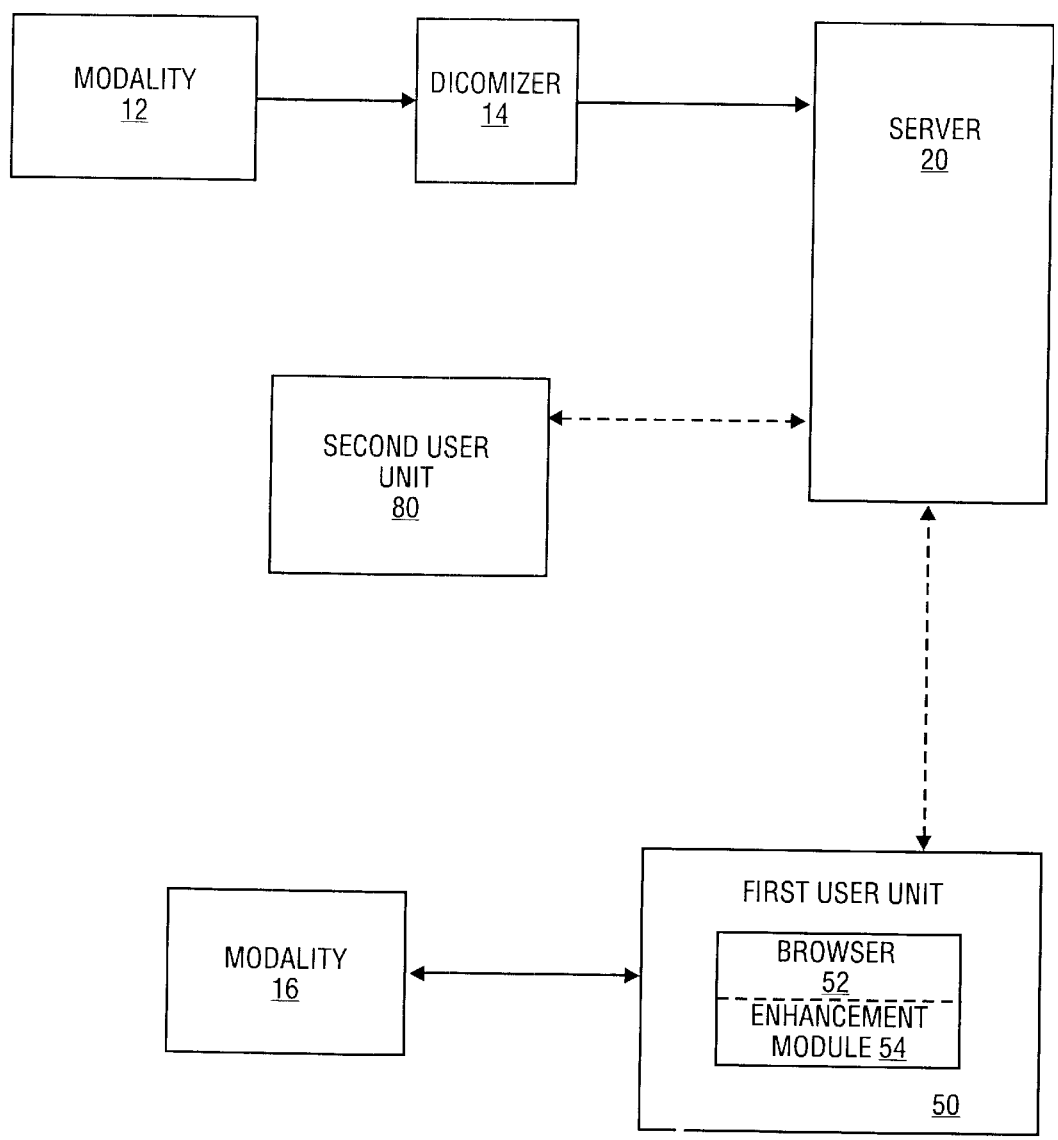
FIG. 1 illustrates one embodiment of a medical information transfer system configured in accordance with the teachings presented herein.

FIG. 1 illustrates an exemplary information transfer system 10 configured in accordance with one embodiment of the present invention. A modality 12 is coupled to a server 20 through a dicomizer 14. A second modality 16 is optionally coupled to a user unit 50, which unit may communicate with the server 20. The user unit 50 may have components to optionally view, manipulate, store and/or print data configured by modality 16 or modality 12. The user unit may transfer such data to the server 20 and/or send the information to another user 80 through the server 20. The other user unit 80 may also communicate with the server 20. It should be noted that the scope of the present invention anticipates any number of modalities, user units and servers configured in accordance herewith and arranged in various fashions.

The modalities 12 and 16 may be any type of device that generates data or data signals related to the examination of a subject. The subject is preferably a human being or an animal, but may also be an inanimate object that is being inspected. The modality may perform the direct examination of the subject, where the modality includes a detection component. Alternatively, the modality may create data or signals from a user's input, where the modality has an input component such as a keyboard, mouse, microphone, etc.

Typically, the modality is a medical device. Medical modalities used in radiology include data acquisition equipment for magnetic resonance imaging (MRI), computed tomography (CT), ultrasound (US), nuclear medicine (NM) and digitized radiography (DR), computer radiography (CR) and digital fluorography. Other modalities include photographic devices such as high resolution digital cameras; sound capture interfaces such as verbal dictation interfaces, Sound Blaster™ interfaces, and the like; video capture interfaces such as Snappy® brand parallel port video capture devices; flatbed scanners and especially Twain compliant acquisition devices such as Visioneer Paperport®. Still other modalities are for angiography, radiography, endoscopy, microscopy, physical exams and waveform devices to collect EEG and/or ECG data, such as from Hewlett Packard Corporation of Palo Alto, Calif. and American Medical Devices Corporation of Lowell, Mass. In addition, the present invention anticipates other modalities and all of the aforementioned modalities are by way of example, and are not intended to limit the choices that are or may become available in the art.

As shown in FIG. 1, the dicomizer 14 receives data from modality 12 and conveys the data to server 20 where it may be processed, stored and/or sent to user units. Dicomizer 14 is an optional component to the information transfer system that converts the raw data into DICOM compliant data. Dicomizer 14 may be a stand-alone device, or alternatively, may be an integral part of a computer system for controlling the operations of the modality.

The server 20 in information transfer system 10 is a computer system that stores medical data and is accessible through a network, e.g., the Internet, an intranet, or an extranet. As shown variously in FIGS. 2A–2D, server 20 has components for handling data in various ways. These components include a data interface (DI) 22 to receive newly acquired data, a processing unit 24 for manipulating the data, a storage unit 30 for retaining (i.e., storing) the data, an assembly unit 32 for gathering together information and an e-mail server 36 for sending the information so gathered. Upon review of this specification, it will be appreciated by those skilled in the art that the components of server 20 may be connected in other ways in addition to those described and shown in FIGS. 2A–2D.

In one embodiment, modality 12 may communicate with the data interface 22 through an Ethernet connection (i.e., the data interface 22 may be an Ethernet port). However, other communication schemes are suitable for transfer of data from modality 12 to server 20, such as serial interfaces, parallel interfaces, RS422 and/or RS432 interfaces, Livewire interfaces, IEEE-1394 serial busses, Appletalk busses, ATM busses and/or networks, token ring and/or other local area networks, universal serial buses, PCI buses and wireless (.e.g, infrared) connections, and the like.

Figures 2A, 2B:
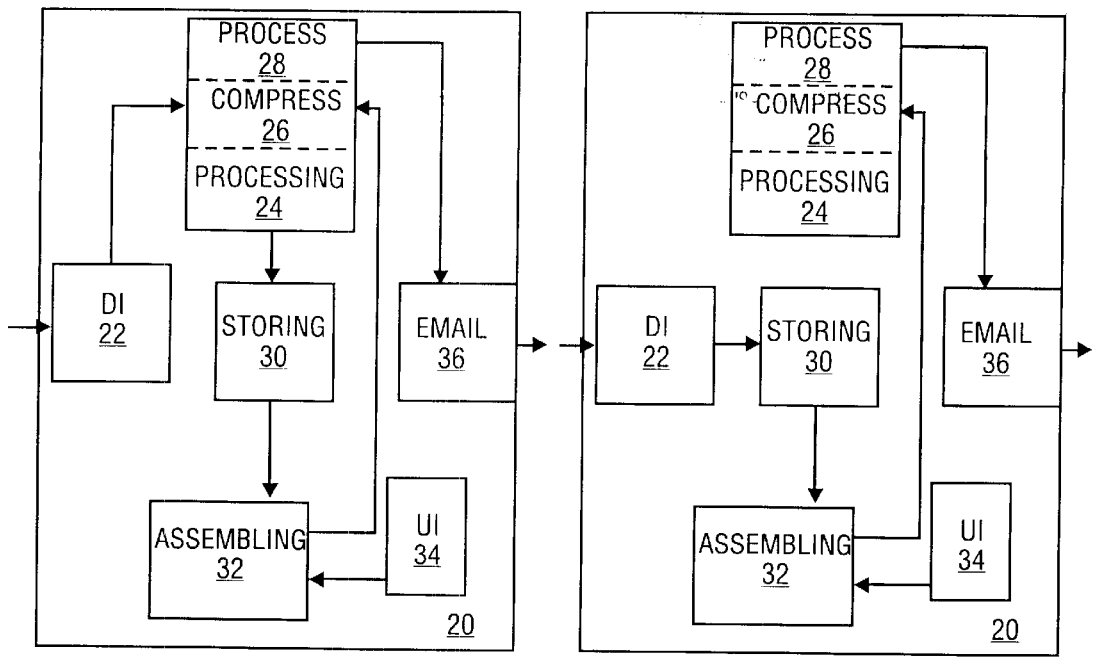

Now referring in more detail to the server components shown in FIG. 2A, a processing unit 24 is coupled in communication with data interface 22. Processing unit 24 provides a mechanism to allow for the compression of data by a compression component 26 prior to storage. For example, processing unit 24 may be a general-purpose processor that transfers data to and from compression component 26. Alternatively, processing unit 24 may be a processor configured to execute instructions defined by compression component 26 (e.g., where compression component 26 is a computer program). The compression of data conserves storage space and/or provides for the speedy transmission of data to the user unit, whereat the browser enhancement module to be described below may be used to decompress the data.

Thus, for one embodiment, the processing unit 24 may use various convenient algorithms that allow data files to shrink in order to compress the data. These algorithms tend to operate by replacing repeating patterns of data with smaller tokens. A header may be added to the data file as it is compressed for containing information necessary in the reconstruction of the file when it is decompressed. In addition, a header may be included which retains information on the way the data was attained and how one data representation, e.g., an image, relates to another representation in the same set of data, e.g., "series 1, image 39 and echo 2."

Generally, compression formats are either high efficiency or low efficiency and either lossless or lossy. Lossy compression schemes are characterized by components of an original image being absent from a reconstructed image after a compression-decompression cycle. Lossless schemes do not drop any information. Compression levels for any scheme may be chosen to be in compliance with the Food and Drug Administration (FDA) requirements for a particular application, e.g., diagnostics or referral quality.

Low compression schemes (i.e., those that do not provide significant compression ratios) that may be used include joint photographic experts group (JPEG) compression schemes that use Fourier analysis-based methods, such as the discrete cosine transform, to compress data; graphics interchange format (GIF) compression schemes, which use LZW algorithms; bitmapped image compression schemes and tagged image file format (TIFF) compression schemes. Alternatively, high efficiency compression schemes, such as wavelet, motion wavelet, Motion Picture Experts Group (MPEG) and/or motion JPEG schemes may be employed. Use of such high efficienciey schemes may be preferred where storage space and/or transmission bandwidth is limited. For example, wavelet compression schemes may be 20 times more efficient than JPEG compression schemes, providing for a more detailed representation of the data at the same bit budget.

In one embodiment, a progressive compression scheme is used prior to storage of data, wherein data is incrementally compressed to varying sizes. An advantage of progressive compression is that where the data is prepared for e-mailing, the server may pull the largest size of data that is capable of being compiled into a package. In this manner, truncation by intermediate mail hosts causing the loss of data segments is avoided. Moreover, the largest acceptable data size also provides the optimal resolution for the data when it is viewed.

Server 20 is further equipped with a storage unit 30 for storing data. In the storage unit 30, data may be constructed into a group of related data to form a file. Such files may contain a compilation of various forms of data from a variety of modalities related to a particular subject or group of subjects.

An assembly unit 32 is coupled to the storage unit 30 for gathering selected medical data and the appropriate user interface pages to form an e-mail package in response to instructions from a remote user unit. The assembly unit 30 pulls appropriate medical data from the storage unit 30 and compiles the data. In one embodiment, the assembly unit 30 only groups the information but does not arrange the information in the order in which it will be viewed by a user unit. Instead, software, e.g., a browser enhancement module, at the user unit rearranges the information for viewing.

A user interface (UI) 34, such as a Web page, is provided to the assembly unit 32 for collection into the e-mail package. The user interface 34 may be a complete or incomplete page. Preferably the interface is an incomplete interface and the remaining portion of the user interface is provided by a browser enhancement module in the user unit. The interface 34 may be a group of interface pages that are connected by hypertext or other links.

The Web page(s) that make up UI 34 may be organized in tree structure, wherein information is arranged hierarchically from general to more specific data. However, the pages may also be arranged in a linear structure, wherein one page leads to the next page, or the pages may be arranged in a random structure. Tree structured Web pages may be used, for example, where an operator is provided with a list of patients' studies. The operator may select from various instances of treatment or separate types of data, e.g., laboratory results, radiology with reports or pathologies. Appropriate related data from an external database may be displayed as part of the selected data.

In the exemplary arrangement shown in FIG. 2A, the assembly unit 32 is further coupled to processing unit 24 to allow for preparation of the e-mail package for sending. Assembling of e-mail packages allows for shorter times for processing, e.g., compressing and encrypting, the e-mail for sending because the entire package is processed as a whole rather than as individual items, which would need to be attached as various components to the e-mail package.

To prepare the package for e-mailing, the compression component 26 of the processing unit 24 may further compress the package into a size that is optimal for e-mailing. As indicated above, one method of achieving the proper compressed data size for e-mail is by adjustable or progressive compression. In such schemes, processing unit 24 may compress the assembled medical data to a default ratio, such as 2:1. The processing unit may then measures the size of the compressed medical data package and compare it to the size that is required by e-mail. The size required by e-mail is that size that allows for the data to be sent without leaving portions of the data behind. Typical requirements for e-mail are about 2 to 3 megabytes. If the current data size is greater than the required size, processing unit 24 compresses the data a second time. The package size is again measured and compared to the required size and this procedure may be repeated until the data size becomes equal to or less than the required size.

An advantage of this adjustable compression scheme is that truncation of data may be avoided. With prior compression schemes, an e-mail package that is larger than the required size typically has sections of the data removed from the e-mailed package. Thus, the recipient only receives a portion of the requested information. Furthermore, adjustable compression allows a variety of modalities to be transferred by e-mail because usually medical files from different modalities have much more data than the acceptable size for e-mail. For example, a typical computed tomography file is about 50 megabytes in size and a computed radiography file is about 10 megabytes in size. Unless these relatively large files are compressed to 2 to 3 megabytes, some of the information is truncated when sent through e-mail. The truncated information is not transferred and the recipient receives only a portion of the file.

Processing unit 24 also has an encoding component 28. The encoding component 28 converts the data into codes acceptable to e-mail. Usually, the data is encoded for Internet transfer by converting the data into an e-mail attachment that is recognized as a MIME binary compliant object. The receiving e-mail application recognizes the MIME encoding and calls the browser enhancement module to decode the attachment.

In some cases the processing unit 24 may include an encryption component to encrypt the data prior to sending it through e-mail. A variety of encryption schemes may be used such as public key encryption or private key encryption. For public key encryption, the server may keep a database of public keys in a key registry (e.g., in storage unit 30). The encoding and/or encrypting components may be stand-alone components or software components (separate or combined) executed by the processing unit 24.

Server 20 also includes an e-mail server 36 coupled to the processing unit 24 and configured to send the e-mail package having the data and at least a partial user interface to user units 50 and 80. The e-mail server breaks messages into packets, e.g., as according to the TCP protocol, and delivers the packets to user units 50, 80, such as with the IP protocol.

In another variation of the server 20, as shown in FIG. 2B, the data interface 22 is not coupled to the processing unit 24. Instead the data interface 22 is coupled to a storage unit 30. In this configuration, the data is not compressed prior to storage, but is compressed after storage in preparation for transmission (e.g., by e-mail).

Figures 2C, 2D:
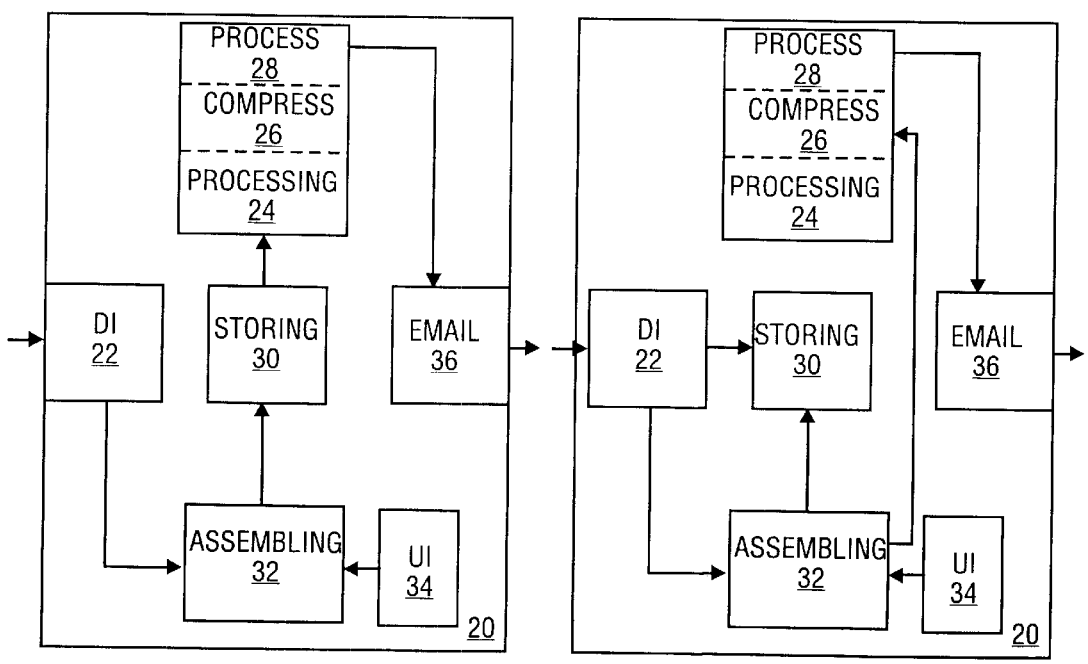

FIGS. 2C and 2D depict further embodiments of the server 20 and its components, where the data interface 22 is coupled to assembly unit 32. In these configurations, data received from the data interface 22 is first assembled into an e-mail package. The packaged information may optionally be placed into storage and then pushed into the processing unit 24 from the storage unit 30 as illustrated in FIG. 2C. Alternatively, FIG. 2D shows that the package may be directly processed for sending by the processing unit 24 and/or stored in storage unit 30. From the server, the user unit receives the requested information.

Figure 3:
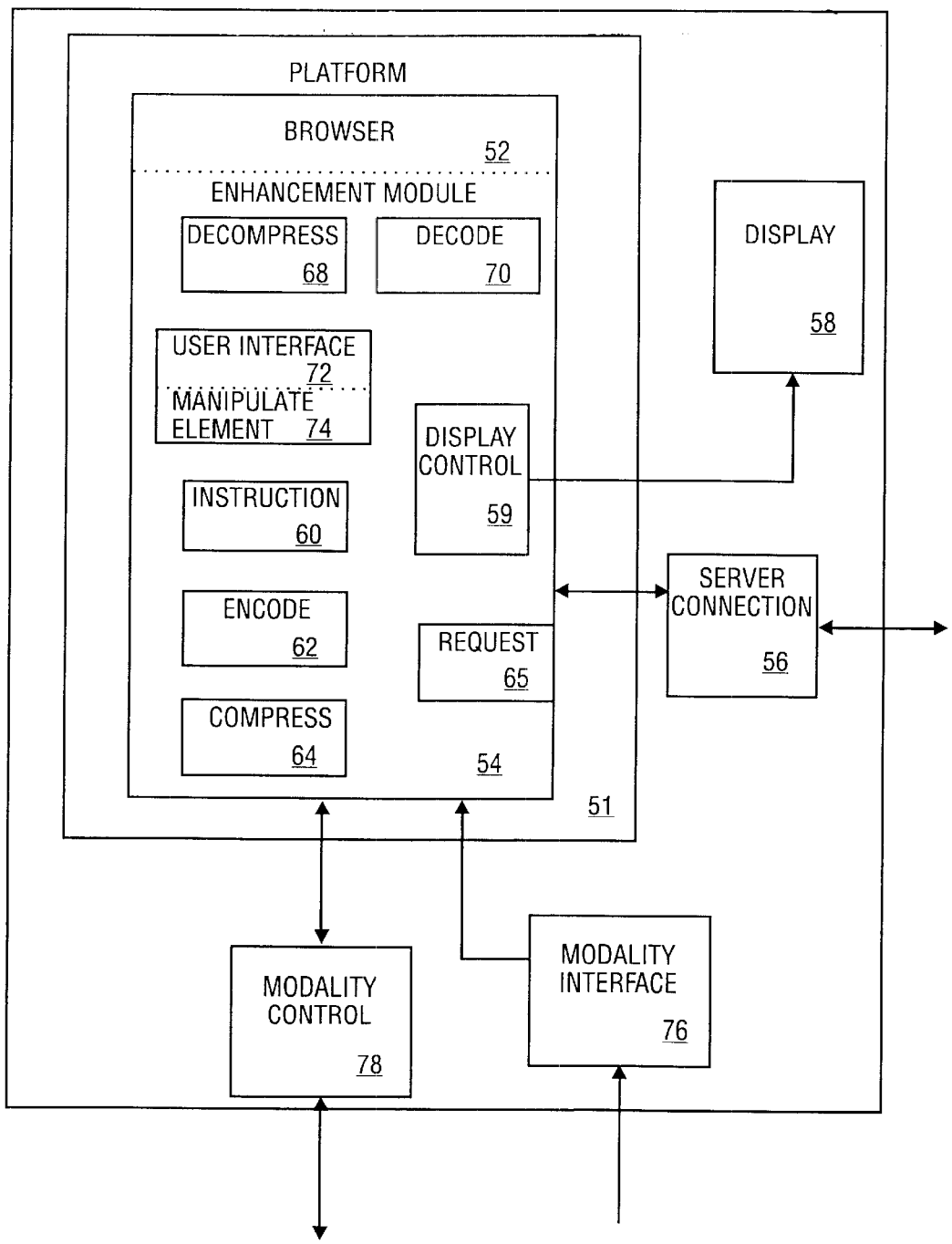
FIG. 3 is a block diagram of one embodiment of a user unit configured in accordance with the teachings presented below.

The user unit 50 and server 20 may be in communication through a variety of connections. FIG. 3 shows one example of a user unit 50 with a server connection 56. Server connection 56 may be a telephone line, local area network (LAN) or wide area network (WAN). The communication link may be also made by a serial line Internet protocol (SLIP), point-to-point protocol (PPP), an online service, an XDSL link, a satellite or other wireless link, a cable modem, an ISDN line, or another communication link. ISDN lines are useful because ISDN is a digital technology using copper cable telephone wires so that there is no need to convert information from digital to analog form prior to transmission. Typically, server connection 56 is an HTTP connection.

User unit 50 includes a platform 51, e.g., a personal computer (PC), such as a Windows™-based PC, Macintosh™, or one of a wide variety of hardware platforms that runs the UNIX™ operating system. The user unit 50 further includes a display 58, which is coupled to the platform 51 through display controller 59. Display 58 may be any one of a number of conventional display devices such as a liquid crystal display or a video display. For sharp colors and grayscale, display 58 is preferably an SVGA monitor, with a resolution of 26 dpi or better, and an active area of at least 17 inches, controlled using a true color video card. The DICOM Standards have also established specific display preferences and the use of DICOM compliant video display devices is contemplated as part of the present invention.

User unit 50 makes use of browser 52, i.e. Web browser software, for communicating with the server 20. The browser 52 issues a request, e.g., an HTTP request, for a particular user interface, e.g., a Web page. The browser 52 is also used in viewing the user interface. Commercially available browsers suited for use in accordance with the present invention include Netscape Navigator™ from Netscape Corporation located in Mountain View, Calif.; Internet Explorer™ from Microsoft Corporation located in Redmond, Wash.; and Lotus Notes™ from Lotus Development Corporation located in Cambridge, Mass.

User unit 50 further includes a browser enhancement module 54 that runs within the browser 52 of the user unit 50. The browser enhancement module 54 performs the necessary tasks to make the data readable or transferable. Because the module is preferably an integral part of the browser, it provides superior capabilities in interacting with the browser and Web, as compared to a helper application, which runs separately from the browser in its own application space. This also provides a convenient way to deliver a completed package of integrated tools to the user's desktop.

Enhancement module 54 may be configured for a particular browser, such as a plug-in for the Netscape Navigator, or an ActiveX control for Microsoft's Internet Explorer or Multipurpose Internet Mail Extensions (MIME) interfaces. Because browser enhancement modules are platform specific, type-specific modules must usually be downloaded according to a particular unit's operating system and processor platform. However, in one embodiment a single enhancement module 54 includes programs for several types of browsers. A detector in the enhancement module determines the type of browser on which the component is being run and then configures itself to be the appropriate software. In this manner the browser enhancement module 54 may be run consistently across all platforms. Furthermore, the browser enhancement module 54 may communicate with the server 20 and may automatically update itself. In this manner, all browser enhancement modules may be consistently revised to be of the latest version. Thus, an advantage of the present data transfer system over those of the past is that the necessity of using a myriad of different software tools or workstations for each type of data generated by various modalities is avoided. All of the necessary components are embedded in the browser enhancement module 54 and the server 20.

Browser enhancement module 54 adds functionality and interactivity to a user interface by integrating code, usually in a seamless manner. The code module appears as extended capabilities of the user interface, undistinguishable from its baseline features. Typical browser enhancement modules provide support for new data types and add operations to the browser. Browser enhancement module 54 is preferably either a full page type or embedded and visible type, but any format is possible.

Browser enhancement module 54 is configured to instruct server 20 as to how to handle particular medical data and files. Depending on the particular application of the transfer system, the server 20 may handle the data in many ways. Instruction component 60 receives requests from the user and directs the server 20 accordingly.

In some cases as depicted in FIG. 3, user unit 50 may generate new data and browser 52 may be used to transfer this new data to the server 20. In such cases, instruction component 60 instructs the server as to what to do with the new data. The new data is information that is not yet stored in the server 20 and may include an alteration to stored data in the server 20. Furthermore, the new data may also be data that had been newly acquired from a medical modality (e.g., modality 16 in FIG. 1) in communication with the user unit 50 or data that has been dragged from the user unit, e.g., retrieval from a hard drive, desktop, or an input interface such as a key board, etc. The dragged data may be dropped into a file for transferring to the server 20.

In order to transfer the new data to the server 20, the encoding component 62 of browser enhancement module 54 codes the data following compression thereof by compressing component 64. The encoding and compressing schemes may be similar to those employed by the server 20 prior to a data transfer and may employ one or more processor(s) of platform 51.

Instruction component 60 may instruct the server 20 to store the new data. In such cases, when the server 20 receives the new data, the data is decoded by processing unit 24 and placed into the server's storage unit 30. The server 20 may also optionally encode the new data in a standard DICOM format prior to such storage.

Instruction component 60 may further (or alternatively) instruct the server to e-mail the new data to a second user unit 80. Although FIG. 1 depicts only two user units, it should be appreciated that any number of user units may receive data from the server 20. The operator of user unit 50 may provide the names or addresses of those user units to receive the data and instruction component 60 may transfer this list to the server 20 with the forwarding instructions. In the alternative, a predefined list of destination user units may be retained in a database either at the user unit 50 or server 20. Optionally, this destination database is automatically updated between related servers.

Instruction component 60 may be further configured to instruct server 20 to merge specific other data with the new data to form an e-mail package, e.g., for forwarding to a second user unit 80. The specific other data may be data already stored in storage unit 30 of server 20, data stored in a remote information system e.g., a hospital information system (HIS) or radiology information system (RIS), data stored in a third party telemedicine package, or the like. Alternatively, the instruction component 60 may instruct server 20 to send only specific other data without any newly added data.

Enhancement module 54 further includes a request component 66 configured to solicit data or other information from the server 20. When such data is received, the data must be processed in order for it to be viewed. Thus, decompression component 68 is included to reconstruct the original file so that it may be used by user unit 50. Decompression component 68 may examine the e-mail package as well as any tokens in the data file to accomplish this result. In addition, a decode component 70 may convert the e-mail into a readable form. If the data was encrypted by the server, then the enhancement module 54 must also decrypt the message.

Enhancement module 54 may also include a user interface 72 with one or more interface pages 73, e.g., Web pages, having various manipulation elements 74 for dictating how the data is viewed within the user interface. In one embodiment, the enhancement module 54 has a portion of a user interface 72 with the manipulation elements 74 and the server 20 has the remaining portion of the user interface. The server 20 transfers its portion of the user interface to the user unit 50 and the enhancement module 54 merges these portions together to form a complete user interface.

Figure 4:
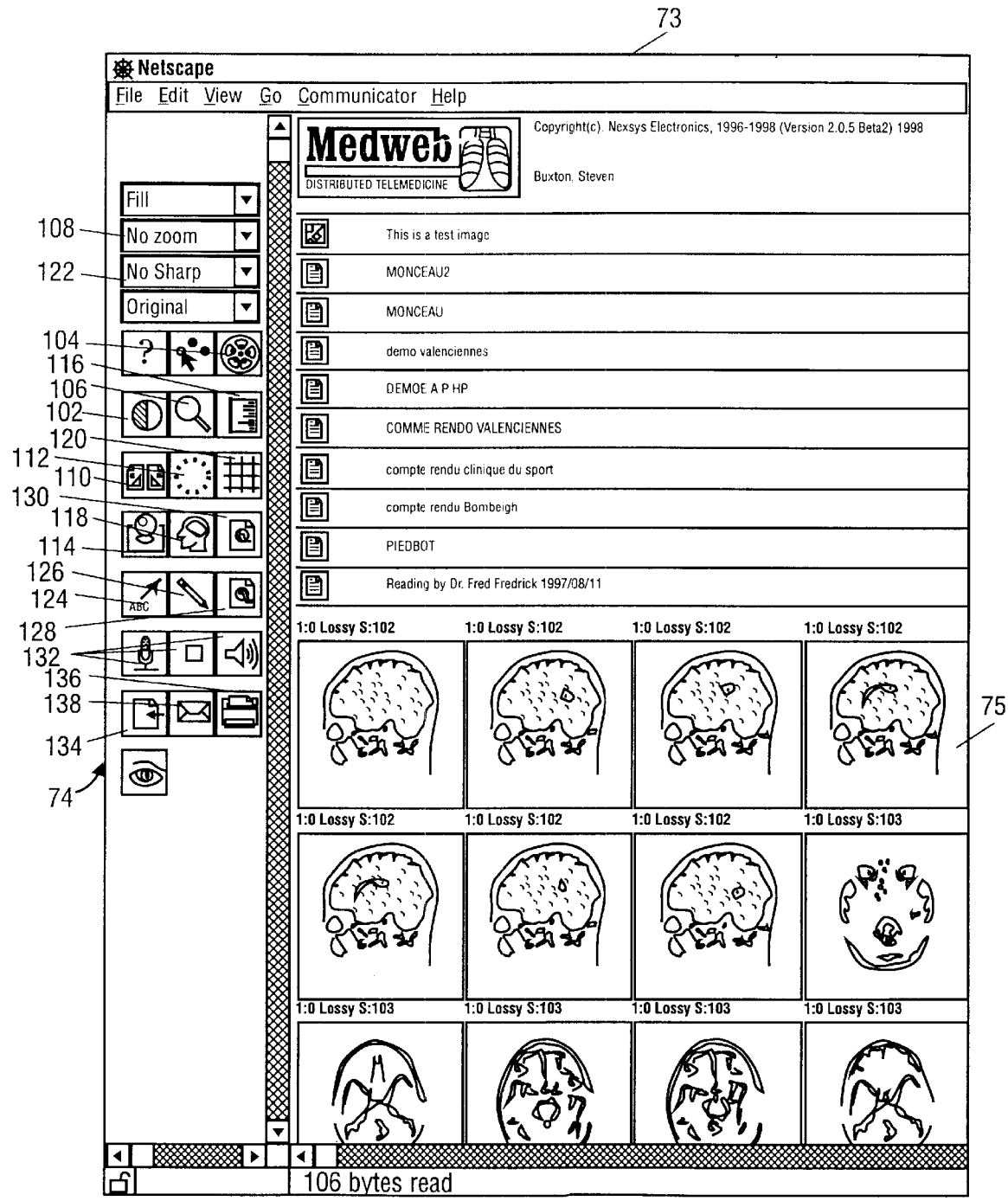
FIG. 4 illustrates one embodiment of a user interface with manipulation elements configured in accordance with the teachings presented herein.

Manipulation elements 74 are used by the operator to alter the display of information or data, typically by selecting the controls as they appear on the user interface with a mouse or other user control device. FIG. 4 illustrates one completed user interface page 73 with a plurality of manipulation elements 74. The enhancement module 54 may provide for any desired number of manipulation elements 74, typically being from 1 to 50, more typically from 4 to 25 and usually at least four elements. It should be appreciated that UI page 73 represents a visual display that may be presented on display 58 (e.g., a screen shot) and which may be created using programming techniques familiar to those of ordinary skill in the art.

One set of manipulation elements 74 is a screen control group for governing the manner in which data fills the screen. Any data format may be viewed, such as images, waveforms, etc. A number index allows the operator to select the number of data representations that occupy the screen. FIG. 4 depicts twelve data representations in the form of radiology images 75 within UI page 73, but any number of representations may be selected. The operator may scroll to obtain subsequent representations in a series of such data in a file. For every representation, the portion that appears within the UI page 73 may be adjusted by a window/level control 102. Using the window/level control 102, the size of the window may be changed and the horizontal level that appears on the display may be altered. Where the server 20 includes an element for fixing the default value for the window and level, the window/level control 102 may vary the setting from its default value. The server 20 optionally includes this window and/or level default element for setting default values in Hounds Field units. When the data is sent to a user unit, it appears on the user's display at the default window and level and control 102 is used to adjust this value.

Another screen control element is a cine control 104, which allows multiple images in a series to be stacked and viewed as fast moving figures layered one on top of the other. The cine control 104 is especially useful for echo in ultrasound data. By applying the cine control 104, an operator may drag a cursor, e.g., using a mouse or other cursor control device, over the image slices to repeatedly flip them in order or reverse order. To further control the display of data, a magnification control 106 provides for enlargement of a region of interest, i.e., a selected portion (e.g., using a magnification boundary under user control) of the image. A zoom control 108 also is provided to increase the size of the entire screen. Conveniently, an operator my select a percentage of zoom, e.g., from 200% to 600%, inclusive, in any of a variety of increments, e.g., increments of 10%, 20%, 25%, 50%, etc.

Another category of controls is a position group for changing the position of an image. Such position changers include a mirror control 110 for obtaining the mirror view of an image. By activating the mirror control 110 an image may be flipped over. The image may be rotated by a rotate control 112, preferably by a quarter turn with each depression of the rotate control 112. In addition, where the server 20 includes an element for converting a 2-D image to 3-D volumes and/or surfaces, a 3-D control 114 may access the 3-D image. The server 20 optionally includes a 3-D volumetric rendering element to depict the internal makeup of a subject and/or surface rendering elements to show the 3-D version of the surface area of a subject. Through the use of these 3-D elements, a 2-D image captured by the server 20 may be converted and stored as a 3-D depiction of the image. This 3-D image may then be e-mailed to a user unit.

Still another set of manipulation elements is the inspection tool set, which facilitates the examination of the images. A measurement control 116 provides linear distances between any given points on an image. In one embodiment, an operator is allowed to drag a cursor over the length of a portion of an image and the measurement control 116 instantly determines the length so traced and displays such measurement to the user. Similarly, the measurement control 116 may also determine the area of a selected region on the image. In a further embodiment, the measurement control 116 may provide the angle of deviation between two selected vectors on the image. The operator may select a first vector and move the cursor, typically with a mouse, from the original vector to a second vector. In this manner, the angle of deviation between the first vector and second vector is presented.

Locator line control 118 is also an inspection tool for a scout view of DICOM MRI images or CT images to show where two images intersect within a study. Other inspection tools may provide the angle, area and/or volume of portions of an image. Furthermore a grid scale control 120 may be used to display a grid over the images, e.g., to be used as a measurement reference. Another control inverts the grayscale of the image so that certain aspects of an image may become more visible. For example, by changing the contrast of an image, certain aspects thereof may stand out because different tissues are displayed with different levels of gray. An edge enhancement control 122 allows an operator to choose the degree of sharpness by digital enhancement of the images and smoothness of the edges of the images.

Still another set of controls is for making annotations to the displayed image. Both an arrow control 124 and a freehand control 126 may be provided for creating lines on an image. Such annotation may be erased by clicking clear control 128, or be hidden from the display, by manipulating hide control 130. A caption control allows for notes to be shown on the screen, especially next to lead lines pointing to certain aspects of the image. Other tools for annotation may be multi-media controls 132 for recording, stopping recording and/or playing back verbal notes.

In one embodiment, the present system provides real time communication between correspondents. Where both correspondents access the same patient records at the same time, each correspondent may select, for example, by clicking a manipulation element, to view each other's annotations and/or to study the manipulations in real time.

After viewing the image, the data may be saved to a local hard drive by save control 134, printed by print control 136 and/or sent to another location via the server 20 by e-mail control 138, as described in detail above. As an added feature, an HL7 report associated with images may be viewed by a report control.

Further to the embodiment shown in FIG. 1, the present system anticipates the optional direct connection of medical modality 16 to user unit 50 through a modality interface 76 (shown in FIG. 3). An application code in the browser enhancement module 54 allows a variety of modalities to be in direct communication with a user unit 50. In this manner, the user unit 50 may capture data from many different data sources. In some embodiments, the modality may be a scanner, a video capture device, a scope, an ECG machine, an ultrasound machine or a digital camera. The modality interface 76 on the user unit 50 may be a serial port, universal serial bus (USB), or the like, depending on the particular connection between the modality 16 and the user unit 50.

In addition, the enhancement module 54 provides for the direct control of the operations of a variety of medical modalities by a modality control unit 78. Through this unit, the user unit 50 may control a plurality of modality operations, such as the settings during data acquisition, on/off, etc., depending, for example, on the type of modality 16 and particular application of the user unit 50. For example, where the modality is a digital camera, the user unit may choose the frames of the film to be uploaded into the user unit 50 and then optionally clear the camera's storage area. In this manner, an operator may perform an examination with the browser enhancement module 54, through a modality 16 from a remote location.

Referring again to FIG. 1, the second user unit 80 may be the recipient of e-mail from the server 20. The second user unit 80 includes an e-mail program that reassembles the messages so that the information can be read, for example, by using TCP protocol. The second user unit 80 may also download the browser and e-mail enhancement module 54 in order to access any transferred images. Although FIG. 1 shows only two user units, in variations of the transfer system 10, any number of user units may communicate with the server 20 in the same manner as user units 50 and 80. Preferably the number of user units is one to several thousand units and more usually about 1 to 100 units.

There are many alternative features that may be added to information transfer system 10 to advance the functionality of the system. Having described the overall system, some optional aspects of the system will now be discussed.

In one alternative/optional embodiment, the server 20 automatically e-mails information to user units on scheduled intervals or whenever new data is received by the server. For example, the server 20 may have a list of users with their patient names. When the server 20 receives data relating to a particular patient, the server 20 identifies the appropriate users to receive the data regarding that particular patient. The server 20 may then automatically send the information to these users as it is received or at predetermined time intervals, for example by transferring to the user units associated with the appropriate users those user interfaces (e.g., Web pages) that have changed since the user's last visit. The data then resides locally on the user unit and may be viewed without first connecting to the server 20. The pages with data may also be viewed more quickly than if the pages were stored only at server 20, because the pages are read at high speed from the user unit's hard drive (or other long term storage device) rather than across slow wires of the Internet or another network.

In another embodiment, server 20 alerts, such as by using alphanumeric pager, a practitioner with the status of incoming data. For example, the server 20 may notify the practitioner when new information regarding a particular patient, has arrived or when a study has been read by another practitioner or is waiting to be read.

The server 20 may also integrate synchronous asymmetric replication (SAR) of data between the databases of multiple servers to create a distributed database architecture between servers. SAR may manage the distribution of information across a wide area network or between two or more servers. The SAR technology may also use complex rules and algorithms to regulate the sequence of data updates and to recover from interruption in communication links between servers in a geographically distributed network.

According to yet a further embodiment, the storage unit 30 in the server 20 may include storage subunits for keeping particular types of data. A clinical storage subunit may be provided for storing clinical medical data and a parameter storage subunit for storing parameter medical data. The parameter subunit may include a header having information relating the parameter data to the appropriate clinical data. Other storage subunits may exist to store various types of data forms. For example, particular subunits may be provided for 3-D volume data, series data, annotation data and background data. However, the storage subunits are optional aspects of the present system. In some embodiments all data is stored in one central storage unit and not individual subunits.

The server 20 may also have a protocol database, especially in the clinical field, to build and retain guidelines which practitioners may follow in collecting the required information for a particular procedure, illness, patient complaint, etc. The guidelines may direct a practitioner to the correct processes in gathering any relevant information such as patient history, physical examinations, laboratory tests, procedures to facilitate a medically sound opinion, and the like. For example, a general practitioner desiring to consult with an orthopedic surgeon about persistent low back pain would select "orthopedic surgery" and then the name of the relevant hospital from a clinical protocol list. In this example, the protocols are listed by chief complaints. By selecting "low back pain," the practitioner is provided with the required tests, history, physical examination data to render a recommendation. These lists are available to a practitioner through e-mail from another practitioner or by uploading the information from the server 20.

The protocols may be gathered from the server 20 through any number of sources. One way to derive the information is by converting existing libraries of clinical protocols from other servers. These other servers may update the present server by using SAR, or the like. In this manner, clinical protocols may be published to all servers in a network for use to any practitioner, especially where a generalist desires to generate a specialty consultation.

Another source of clinical protocols is by a Web-based author interface allowing a practitioner to publish the protocols to a server. The author interface is preferably built into the browser enhancement module 54, but may also be located on the server 20. The interface allows an operator to start from a generalized framework of the protocol to be created or to be edited and republished. A completed protocol is published to the server and becomes the protocol of choice for that topic, when addressed to a particular practitioner, institution, the entire healthcare system, etc.

The author interface allows practitioners to provide instant improvements to clinical protocols, publish new protocols, retire obsolete protocols, etc., without having to intervene with current software programs. By internalizing the interface into the browser enhancement module, the application is not restricted by current browser technology limitations, such as the ability to create new fields in the clinical protocols.

In alternative embodiments of the user unit 50, an e-mail server may be located in the user unit for viewing mail sent from the server 20 to the user unit 50. Furthermore, the user unit 50 may have an e-mail enhancement module which has attributes similar to those described above with respect to the browser enhancement module to enhance viewing of the user interface. Such an enhancement module is especially useful for MIME compliant e-mail servers. However, the e-mail component need not send instructions from the user unit 50 to the server 20, rather the e-mail component need only retrieve messages.

Thus, the present information transfer system builds upon the browser, browser enhancement module and e-mail component of the server, as each described above, to provide an interactive collaboration between consultants by linking their actions, annotations and dictations on the same patient. The system allows the correspondent to save a scripted multimedia annotation to a patient folder and upload it to the server or e-mail it with the study to another correspondent. The other correspondent may then play back the annotation and then respond with his own.

The present invention has been described above in varied detail by reference to the particular embodiments and figures. However, these specifics should not be construed as limitations on the scope of the invention, but merely as illustrations of some of the presently preferred embodiments. It is to be further understood that other modifications or substitutions may be made to the described information transfer system as well as methods of its use without departing from the broad scope of the invention. Therefore, the scope of the invention should be determined by the following claims and their legal equivalents.

What is claimed is:

1. A medical information transfer server comprising:
    A) a data interface for acquiring medical data in a multimedia format;
    B) a storage unit coupled to receive and store the multimedia medical data from the data interface;
    C) at least a portion of a user interface to allow for viewing the multimedia medical data;
    D) an assembly unit coupled to the user interface and the storage unit or to the data interface, the assembly unit to gather selected portions of the multimedia medical data to form an e-mail package in response to an instruction received from a remote first user unit;
    E) a processing unit coupled to the assembly unit or to the data interface and to encode and/or compress the multimedia medical data; and
    F) an e-mail server to send by e-mail the user interface and the e-mail package to a remote second user unit.

2. The medical information transfer server of claim 1, wherein the multimedia medical data comprises image, overlay, 3-D volume, waveform, curve, video, and/or sound data, or any combination thereof.

3. The medical information transfer server of claim 1, wherein the selected portions of the multimedia medical data are gathered from the storage unit.

4. The medical information transfer server of claim 1, wherein the selected portions of the multimedia medical data include new data received from the data interface.

5. The medical information transfer server of claim 1, wherein the selected portions of the multimedia medical data include new data received from the remote first user unit.

6. The medical information transfer server of claim 1, wherein the user interface comprises a Web page.

7. The medical information transfer server of claim 1, wherein the processing unit is further to encrypt the multimedia medical data.

8. The medical information transfer server of claim 1, wherein the processing unit is to compress the multimedia medical data using a progressive compression scheme prior to sending the e-mail package.

9. The medical information transfer server of claim 1, wherein the processing unit is to compress the multimedia medical data using at least one of a wavelet, a motion wavelet, an MPEG or a motion JPEG compression scheme.

10. The medical information transfer server of claim 1, wherein the processing unit is to compress the multimedia medical data by:
    (i) compressing the medical data to a default ratio;
    (ii) measuring the size of the compressed multimedia medical data;
    (iii) comparing the size of the compressed multimedia medical data to a required size; and
    (iv) repeating (i) through (iii) using the compressed medical data until the compressed multimedia medical data achieves the required size or smaller prior to sending the e-mail package.

11. The medical information transfer system of claim 1, wherein the multimedia medical data includes clinical data and parameter data.

12. The medical information transfer system of claim 11, wherein the data storage unit includes a clinical data storage subunit for storage of the clinical data and a parameter data storage subunit for storage of the parameter data.

13. The medical information transfer system of claim 1, wherein the server further comprises a 3-D volumetric rendering element and 3-D surface rendering element to convert 2-D images into 3-D images.

14. The medical information transfer system of claim 1, wherein the server further comprises a window and/or level element(s) for establishing window and/or level default values.

15. The medical information transfer system of claim 1, wherein the server further comprises an automatic e-mail control to direct the e-mail server to automatically send new medical data to the remote first user unit at prescribed intervals.

16. A medical information transfer unit comprising:
    A) a display for viewing a medical file on a user interface having at least one manipulation element for view control of the medical file, and
    B) a browser for communicating with a server having stored therein a plurality of medical files containing multimedia medical data, the browser including a browser enhancement module to:
        (i) request the medical file from the server;
        (ii) decompress and/or decode the medical file after receipt from the server;
        (iii) transfer the medical file to the display; and
        (iv) send instructions to the server to assemble and to e-mail selected multimedia medical data from the medical file and at least a portion of a user interface stored on the server to a remote user unit separate from the information transfer unit.

17. The medical information transfer unit of claim 16, wherein the browser enhancement module comprises a plug-in or ActiveX control.

18. The medical information transfer unit of claim 16, wherein the browser enhancement module is further to decrypt the medical file after receipt from the server.

19. The medical information transfer unit of claim 16, wherein the medical file includes clinical data, parameter data, series data, annotation data, observation data, 3-D volume data, and/or combinations thereof.

20. The medical information transfer unit of claim 16, wherein the browser enhancement module is further to instruct the server to assemble the selected data with new data to form an package and to e-mail the package to the remote user unit.

21. The medical information transfer unit of claim 20, wherein the transfer unit further comprises a modality interface for acquiring the new data.

22. A medical information transfer system, comprising:
A) a server storing multimedia medical data, the server comprising:
  i) a data interface for acquiring the multimedia medical data;
  ii) a storage unit coupled to receive and store the multimedia medical data from the data interface into medical files;
  iii) at least a portion of a user interface for viewing the multimedia medical data;
  iv) an assembly unit coupled to the user interface and the storage unit or to data interface, the assembly unit to gather selected portions of the multimedia medical data to form an e-mail package in response to instructions received from a first user unit;
  v) a processing unit coupled to the assembly unit or to the data interface and to encode and/or compress the multimedia medical data; and
  vi) an e-mail server to send by e-mail the at least portion of the user interface and the e-mail package to a second user unit.
B) the first user unit comprising:
  i) a display for viewing at least a first one of the medical files using a user interface having at least one manipulation element for view control of the first medical file, and
  ii) a browser for communicating with the server, the browser including a browser enhancement module to:
    a) request the first medical file from the server;
    b) decompress and/or decode the first medical file;
    c) transfer the first medical file to the display; and
    d) send instructions to the server to assemble and to e-mail the selected portions of the multimedia medical data from the first medical file and the at least portion of the user interface to the second user unit.

23. The medical information transfer system of claim 22, wherein the browser enhancement module is further to decrypt the first medical file.

24. The medical information transfer system of claim 22, further comprising a medical modality for generating the multimedia medical data.

25. The medical information transfer system of claim 24, wherein the medical modality comprises radiology equipment.

26. The medical information transfer system of claim 22, further comprising at least two different types of medical modalities for generating the multimedia medical data.

27. The medical information transfer system of claim 24, wherein the medical modality is communicatively coupled to the data interface for transmitting the multimedia medical data to the server.

28. The medical information transfer system of claim 27, wherein the medical modality is communicatively coupled to the data interface through a dicomizer to convert raw multimedia medical data provided by the medical modality into multimedia medical data of a form compliant with the DICOM Standards.

29. The medical information transfer system of claim 24, wherein the medical modality is communicatively coupled to the first user unit, and wherein the browser enhancement module is further to encode data received from the medical modality.

30. The medical information transfer system of claim 22, wherein the browser enhancement module is further to encrypt the multimedia medical data.

31. The information transfer system of claim 29, wherein the browser enhancement module is further configured to direct more than one operation of the medical modality.

32. The medical information transfer system of claim 29, wherein the browser enhancement module is further to encrypt the data received from the medical modality.

33. The medical information transfer system of claim 22, wherein the processing unit is to compress the multimedia medical data using at least one of a wavelet, a motion wavelet, an MPEG or a motion JPEG compression scheme.

34. The medical information transfer system of claim 22, wherein the processing unit is to compress the multimedia medical data by:
  I) compressing the multimedia medical data to a default ratio;
  II) measuring the size of the compressed multimedia medical data;
  III) comparing the size of the compressed multimedia medical data to a required size; and
  IV) repeating (I) through (III) using the compressed multimedia medical data until the compressed multimedia medical data achieves the required size or smaller prior to sending the e-mail package.

35. The medical information transfer system of claim 22, wherein the server further comprises an automatic e-mail control to direct the e-mail server to automatically send new multimedia medical data to the first user unit at prescribed intervals.

36. The medical information transfer system of claim 35, wherein the server further comprises a mailing list of users designated to automatically receive the new multimedia medical data.

37. A computer readable medium having stored therein a plurality of sequences of instructions, which, when executed by a processor, cause the processor through a browser to:
A) request from a server a medical file for viewing with a user interface having at least one manipulation element for view control of the medical file, the server having stored therein medical files containing multimedia medical data;
B) decompress and/or decode the medical file;
C) transfer the medical file to a display; and
D) e-mail instructions to the server to assemble and send by e-mail selected multimedia medical data from the medical file and at least a portion of the user interface from the server to a remote user unit separate from the processor.

38. The computer readable medium of claim 37, wherein the multimedia medical data is in the form of image, overlay, 3-D volume, waveform, curve, video or sound data, or any combination thereof.

39. The computer readable medium of claim 37, further including additional steps, which, when executed by the processor, cause the processor to decrypt the medical file.

40. The computer readable medium of claim 37, wherein the decompressing is performed using a wavelet, a motion wavelet or a motion JPEG decompressing scheme.

41. Computer readable instructions, which when executed cause a processor to:
A) request from a server a medical file viewable using a user interface having at least one manipulation element for view control of the medical file, the server having stored therein medical files containing multimedia medical data;

B) decompress and/or decode the medical file;

C) transfer the medical file to a display; and

D) e-mail instructions to the server to assemble and e-mail selected multimedia medical data from the medical file and at least a partial user interface from the server to a remote user unit separate from the processor.

42. The computer readable instructions of claim 41, wherein the multimedia medical data is in the form of image, overlay, 3-D volume, waveform, curve, video or sound data, or any combination thereof.

43. A series of computer readable instructions embodied as data signals in a carrier wave, which when executed cause a processor through a browser to:

A) request from a server a medical file viewable using a user interface having at least one manipulation element for view control of the medical file, the server having stored therein medical files containing multimedia medical data;

B) decompress and/or decode the medical file;

C) transfer the medical file to a display; and

D) e-mail instructions to the server to assemble and e-mail selected multimedia medical data from the medical file and at least a partial user interface from the server to a remote user unit separate from the processor.

44. The series of computer readable instructions of claim 43, wherein the multimedia medical data is in the form of image, overlay, 3-D volume, waveform, curve, video or sound data, or any combination thereof.

45. A method, comprising:

A) receiving new medical data through a browser enhancement module;

B) encoding and/or compressing the new medical data using the browser enhancement module;

C) sending the new medical data to a server; and

D) instructing the server to e-mail a medical file having the new medical data and selected stored multimedia medical data and at least a partial user interface to a second user unit.

46. The method of claim 45, wherein the new medical data is received from a medical modality to be controlled using the browser enhancement module.

47. The method of claim 45, further comprising encrypting the new medical data after compressing the new medical data.

48. The method of claim 45, wherein the new medical data is compressed using one of a wavelet, a motion wavelet or a motion JPEG compression scheme.

49. The method of claim 45, wherein the new medical data is compressed using a progressive compression scheme wherein:

A) the new medical data is compressed to provide compressed medical data;

B) the size of the compressed medical data is compared to a required size; and

C) steps A and B are repeated using the compressed medical data until the size of the compressed medical data is the required size or smaller.

50. A series of computer readable instructions embodied as data signals in a carrier wave, which when executed cause a processor through a browser to perform the steps of:

A) receiving new multimedia medical data from a medical modality;

B) encoding the new multimedia medical data;

C) compressing the new multimedia medical data;

D) requesting from a server, a user interface having at least one manipulation element for viewing control of the new multimedia medical data; and E) transferring the new multimedia medical data onto the user interface and sending the new multimedia medical data and user interface to the server.

51. The series of computer readable instructions of claim 50, further including instructions to cause the processor to direct the operation of the medical modality.

52. The series of computer readable instructions of claim 50, further including instructions to cause the processor to select stored medical data from the server and to direct the server to assemble the new multimedia medical data with the selected stored data and electronic mail a medical file including both the new multimedia medical data and the selected stored medical data to a remote user unit.

53. The series of computer readable instructions of claim 50, wherein the new multimedia medical data is in the form of image, overlay, 3-D volume, waveform, curve, video or sound data, or any combination thereof.

54. The series of computer readable instructions of claim 50, further including instructions which cause the processor to encrypt the new multimedia medical data after compressing the new multimedia medical data.

55. The series of computer readable instructions of claim 54, wherein the new multimedia medical data is compressed using one of a wavelet, a motion wavelet or a motion JPEG compression scheme.

56. The series of computer readable instructions of claim 50, wherein compressing the new multimedia medical data includes the steps of:

A) compressing the new multimedia medical data to a default ratio to achieve compressed data;

B) measuring the size of the compressed data;

C) comparing the size of the compressed data to a required size;

D) further compressing the compressed data if the size is greater than the required size;

E) repeating steps B to D until the size of the compressed data is the required size or smaller.

57. The series of computer readable instructions of claim 50, wherein the at least one manipulation element on the user interface is a 3-D control and the server further has a 3-D volumetric rendering element and 3-D surface rendering element for converting 2-D images into 3-D images.

58. A server, comprising:

A) a data interface for acquiring clinical multimedia medical data and parameter medical data;

B) a clinical data s torage unit coupled to the data interface and to receive the clinical multimedia medical data;

C) a parameter data storage unit coupled to the data interface and to receive the parameter medical data;

D) at least a portion of a user interface for viewing the clinical multimedia medical data;

E) an assembly unit coupled to the user interface and the storage unit or to the data interface, the assembly unit to gather selected portions of the clinical multimedia medical data and the parameter medical data to form an e-mail package in response to instructions from a first user unit;

F) a processing unit coupled to the assembly unit or to the data interface and to encode and/or compress the clinical multimedia medical data and the parameter medical data; and G) an e-mail server to send by e-mail the at least portion of user interface and the e-mail package to a second user unit.

* * * * *